(12) United States Patent
Janusson et al.

(10) Patent No.: US 8,410,331 B2
(45) Date of Patent: *Apr. 2, 2013

(54) ABSORBENT STRUCTURE IN AN ABSORBENT ARTICLE

(75) Inventors: Hilmar Janusson, Seltjarnarnesi (IS); Palmar I. Gudnason, Mosfellsbaer (IS)

(73) Assignee: Ossur HF, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 13/238,267

(22) Filed: Sep. 21, 2011

(65) Prior Publication Data

US 2012/0010583 A1    Jan. 12, 2012

Related U.S. Application Data

(63) Continuation of application No. 12/917,565, filed on Nov. 2, 2010, now Pat. No. 8,026,406, which is a continuation of application No. 11/979,758, filed on Nov. 8, 2007, now Pat. No. 7,842,848.

(60) Provisional application No. 60/858,371, filed on Nov. 13, 2006.

(51) Int. Cl.
*A61F 13/00*    (2006.01)

(52) U.S. Cl. ............................. 602/46; 602/47; 602/56

(58) Field of Classification Search ............... 602/41–56
See application file for complete search history.

(56) References Cited

U.S. PATENT DOCUMENTS

| | | | |
|---|---|---|---|
| 3,301,257 A | 1/1967 | Crowe et al. | |
| 4,550,125 A | 10/1985 | Lee et al. | |
| 4,572,814 A | 2/1986 | Naylor et al. | |
| 4,613,630 A | 9/1986 | Bauman et al. | |
| 4,660,553 A | 4/1987 | Naylor et al. | |
| 4,719,243 A | 1/1988 | Pocknell | |
| 4,760,098 A | 7/1988 | Miutel | |
| 4,762,859 A | 8/1988 | Modic et al. | |
| 4,767,794 A | 8/1988 | Modic et al. | |
| 4,808,634 A | 2/1989 | Uriarte et al. | |
| 4,838,253 A | 6/1989 | Brassington et al. | |
| 5,010,115 A | 4/1991 | Grisoni | |
| 5,153,231 A | 10/1992 | Bouquet et al. | |
| 5,436,274 A | 7/1995 | Sumpter et al. | |
| 5,573,994 A | 11/1996 | Kabra et al. | |
| 6,036,997 A | 3/2000 | Ragland et al. | |
| 6,051,747 A | 4/2000 | Lindqvist et al. | |
| 6,207,875 B1 | 3/2001 | Lindqvist et al. | |
| 6,399,854 B1 | 6/2002 | Vartiainen | |
| 6,586,483 B2 | 7/2003 | Kolb et al. | |
| 6,657,101 B1 | 12/2003 | Malmgren et al. | |
| 6,923,834 B2 | 8/2005 | Karason | |
| 6,936,073 B2 | 8/2005 | Karason | |
| 6,998,510 B2 | 2/2006 | Buckman et al. | |
| 8,026,406 B2 * | 9/2011 | Janusson et al. ................ | 602/46 |
| 2002/0193723 A1 | 12/2002 | Batdorf, Sr. et al. | |
| 2003/0180281 A1 | 9/2003 | Bott et al. | |
| 2003/0204159 A1 | 10/2003 | Lawry | |
| 2004/0009725 A1 * | 1/2004 | Yahiaoui et al. .............. | 442/118 |
| 2004/0241215 A1 | 12/2004 | Lipman | |

\* cited by examiner

*Primary Examiner* — Michael A. Brown

(74) *Attorney, Agent, or Firm* — Bacon & Thomas, PLLC

(57) ABSTRACT

An absorbent structure comprising a silicone foam having pore walls and a plurality of hydrophilic particles anchored to the pore walls of the foam. Some of the hydrophilic particles have an anchored portion firmly anchored to the pore walls and an exposed portion extending outwardly away from the pore walls upon which the anchored portion is secured.

17 Claims, 2 Drawing Sheets

ABSORBENT STRUCTURE IN AN ABSORBENT ARTICLE

This application is a continuation of U.S. application Ser. No. 12/917,565 filed on Nov. 2, 2010, which is a continuation of U.S. application Ser. No. 11/979,758 filed on Nov. 8, 2007, which claims the benefit of priority from U.S. provisional application No. 60/858,371, filed on Nov. 13, 2006.

FIELD OF THE INVENTION

The present invention relates to a monolithic absorbent structure having a facing layer for use in an absorbent article such as a wound dressing, hygiene product, prosthetic device or orthopedic device. More particularly, the absorbent article includes a silicone foam having pores and a plurality of hydrophilic particles anchored to the pore walls of the foam.

BACKGROUND

Occlusive or moisture-retentive dressings have gained increasing acceptance in treating wounds, in particular pressure sores and ulcers. A wide variety of types of structures are known in the art for use in or as wound dressings, and generally comprise components for receiving, absorbing and retaining exudate. Typically, these dressings include polymeric foams, polymeric films, particulate and fibrous polymers, hydrogels and hydrocolloids. Dressings with at least one of these components promote wound healing by providing a moist environment, while removing excess exudate and toxic components, and further serve as a barrier to protect the wound from secondary bacterial infection. While these known dressings can effectively manage a wound, many have been found to possess certain limitations or disadvantages.

Many known dressings possess the disadvantage of relying solely on a pressure sensitive adhesive layer to secure the dressing to skin. An example of an adhesive is an acrylate glue. While indeed an acrylate glue securely maintains a dressing over a wound, the glue has a tendency to strip the central portion of the dressing from the wound and thus may damage healing tissue.

Many of the known dressings have an absorbent layer that comprises hydrophilic polymeric foam. Unfortunately, many hydrophilic polymeric foam dressings possess the disadvantage of being limited in the amount of exudate that may be absorbed. The limit in exudate absorption of the foam is often directly related to its overall geometrical size prior to absorbing a fluid. Typically, hydrophilic foams may expand only to 10-20% of their original size.

Another disadvantage to hydrophilic foam dressings is that a certain amount of exudate can be "squeezed" out of the foam due to poor liquid retention. The ability of exudates to be squeezed from the foam, and thus the dressing itself, poses a risk of infection and may interfere with the healing of the wound.

Yet another disadvantage with known foam dressings is that absorption of exudate by an absorptive layer, such as foam, in contact with the wound causes the central portion of the applied dressing to swell and push up against the wound. Continued swelling can induce separation of the skin adherent layer from the skin outside the wound area, especially at the border of the wound dressing whereat a "curling" effect may occur. This excessive swelling of the dressing may further lead to leakage of the exudate from the periphery of the dressing, thereby providing a tract for the invasion of pathogenic microorganisms and promoting maceration of the wound site.

Still another disadvantage of hydrophilic foam dressings is that, as cellular tissue grows during the healing process, the cellular tissue may firmly bind to the wound dressing. This is especially the case when the foam dressing has a coarse and porous exterior surface into which cellular tissue will grow. Removing the wound dressing when it is adhered to the wound in this manner will likely traumatize the wound and cause additional pain to the patient. Repeated changing of the wound dressing will result in repeated traumatization of the wound and will ultimately increase the time needed for the wound to completely heal.

For the foregoing reasons, there is a demand for an absorbent structure which prevents wound trauma upon repeated dressing changes, improves the durability and lifetime of the dressing, anatomically conforms to a body portion bearing a wound, possesses suitable fluid uptake, retention and removal properties, and can be securely maintained on a patient's body. It is also desirous to provide an absorbent structure that has suitable absorption properties while dispensing with the need to secure a skin adherent facing layer to the absorbent structure.

A demand also exists for absorbent articles for use in managing moisture in prosthetic devices and for delivering drugs to the body which have similar properties as those described above, such as suitable fluid uptake, retention and removal, and secure placement and anatomical conformance with a body.

SUMMARY

The present invention is directed to embodiments of a monolithic absorbent structure having an apertured facing layer for use in an absorbent article and methods of making the same.

According to one embodiment, an absorbent structure includes an open-cell silicone foam having pore walls. In another embodiment, the absorbent structure may include a closed-cell silicone foam having pore walls. In still another embodiment, the silicone foam is partially a closed-cell silicone foam having pore walls and partially an open-cell silicone foam having pore walls.

A plurality of hydrophilic particles is anchored to the pore walls of the foam. At least some of the hydrophilic particles have an anchored portion firmly anchored to the pore walls and an exposed portion extending outwardly away from the pore wall upon which the anchored portion is anchored.

In one variation of the embodiment, the silicone foam defines opposed first and second surfaces. The first surface of the silicone foam has skin-adherent properties thereby defining a facing layer. The facing layer of the silicone foam may include a plurality of apertures arranged in a pattern, and the apertures may have a generally uniform structure.

According to one construction of the absorbent structure, the silicone foam forms a liquid retention portion within the thickness of the silicone foam, and a skin-adherent portion underlying the liquid retention portion and generally defined along a first foam surface. In one variation of this construction, the pore walls of the liquid retention portion may be more cross-linked than the skin-adherent portion of the silicone foam such that the skin-adherent portion is tacky to human skin.

By way of example, the hydrophilic particles may amount to being 5%-30% by weight of the total weight of the silicone foam in a dry condition.

Embodiments of the absorbent structure may be provided in an absorbent article including the absorbent structure, and a vapor permeable, liquid impervious backing layer secured to the second surface of the silicone foam.

The absorbent structure may be made by using the following method:

(1) providing an absorbent powder of 5%-30% of weight of the total weight of the absorbent structure in a dry condition;

(2) providing a wet powder which is 3% w/w powder in an aqueous solution;

(3) preparing an uncured mixture including the absorbent powder, the wet powder and an uncured silicone compound; and (4) curing the mixture at a predetermined temperature for a predetermined period of time.

Additionally, the method may include the steps of applying the uncured mixture onto a mold having a plurality of projections arranged in a pattern to thereby impart a plurality of apertures on one surface of the absorbent structure. The mold may also produce an absorbent structure that can accommodate a device or part of a device, such as by providing a cavity in the absorbent structure.

By heating the mixture, the silicone foam is cross-linked. The curing of the mixture may be adapted so that the pore walls of the liquid retention portion are more cross-linked than the skin-adherent portion of the silicone foam. By reducing the degree of cross-linking the skin-adherent portion of the silicone, the skin-adherent portion of the silicone foam may have an elastomeric consistency so as to minimize trauma when the absorbent structure is applied over or removed from a wound.

BRIEF DESCRIPTION OF THE DRAWINGS

These and other features, aspects, and advantages of the present invention will become better understood with regard to the following description, appended claims, and accompanying drawings where:

DETAILED DESCRIPTION OF VARIOUS EMBODIMENTS

Figure 1:
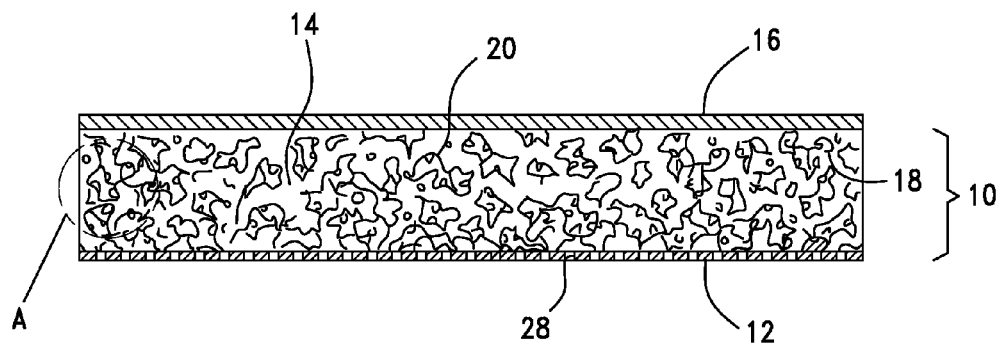
FIG. 1 is a side elevational view showing an embodiment of an absorbent article having the absorbent structure.

As shown in FIG. 1, a monolithic absorbent structure 10 includes an open-cell silicone foam 14 having pore walls 18. In the open-cell configuration, the pores of the silicone foam are interconnected and create an interconnected network of passages throughout the silicone foam. A plurality of hydrophilic particles 20 are anchored to the pore walls 18 of the open-cell foam 14. The absorbent structure 10 includes a facing layer 12 that defines a plurality of apertures 28 formed along one of two opposed sides of the absorbent structure 10. The open-cell foam 14 generally forms a liquid retention portion of the absorbent structure, whereas the facing layer 12 generally forms a generally skin-adherent portion. The absorbent structure 10 may also optionally comprise a backing layer 16.

In an alternate configuration, the silicone foam is a closed-cell silicone foam. In the closed-cell silicon foam configuration, the aforementioned pores are not connected to each other and thus do not form part of an interconnected network.

In still another configuration, the silicone foam is partially a closed-cell silicone foam and partially an open-cell silicone foam. In this configuration, some of the pores are connected and form an interconnected network, while some of the pores are not part of any interconnected network.

The absorbent structure functions so that as the absorbent structure is placed on a wound or is exposed to moisture (such as perspiration in a prosthetic device), the moisture is pressed or flows through the apertures of the facing layer and comes into contact with the exposed portions of the hydrophilic particles, which in turn absorb the moisture. Since the silicone foam is generally hydrophobic in nature, it generally does not absorb moisture. Instead, the hydrophilic particles lock the moisture in the absorbent structure.

As is well understood, silicone is a hydrophobic material. Embodiments described herein employ hydrophobic silicones. An exemplary silicone mixture for making the silicone foam comprises MED-4901 manufactured by NuSil Technology, LLC.

Figure 4:
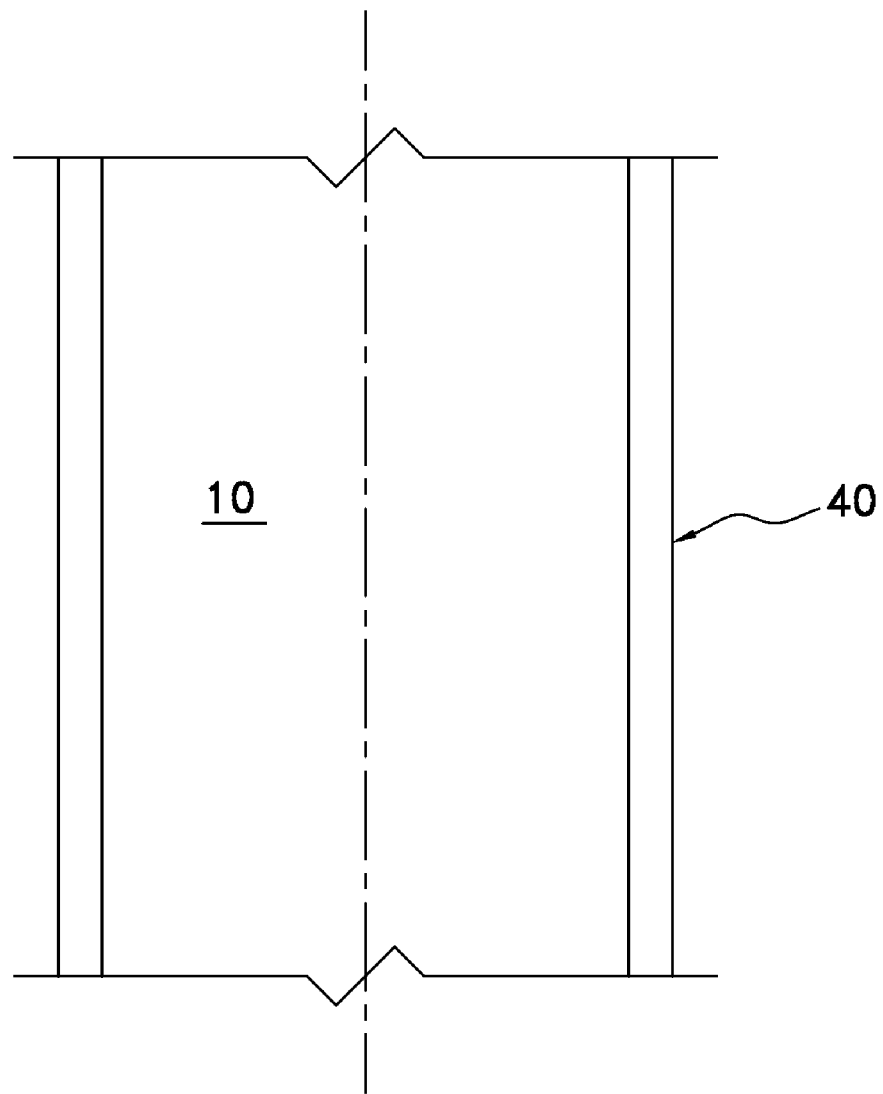
FIG. 4 is a schematic view showing the absorbent article in the form of an inner sleeve.

The shape and size of the absorbent structure is not limited. The absorbent structure may be shaped and sized based on the intended application of the absorbent structure. For example, when used as a wound dressing, the absorbent structure may be cut to a size equal to or slightly greater than the wound, such that the wound is covered by the absorbent structure. In this manner, the absorbent structure serves as a barrier to secondary bacterial infection. As shown in FIG. 4, when used in a prosthetic device, the absorbent article 10 may be shaped in the form of the inner sleeve 40 of the prosthetic device which comes into contact with a residual limb where perspiration may form. In this manner, the absorbent structure serves to move moisture away from the interface between the residual limb and the prosthetic device, thereby reducing the chance for slippage. When used for drug delivery, the absorbent structure may be shaped in any size necessary for carrying a suitable amount of drug to be delivered to a targeted area of the body.

Figure 2:
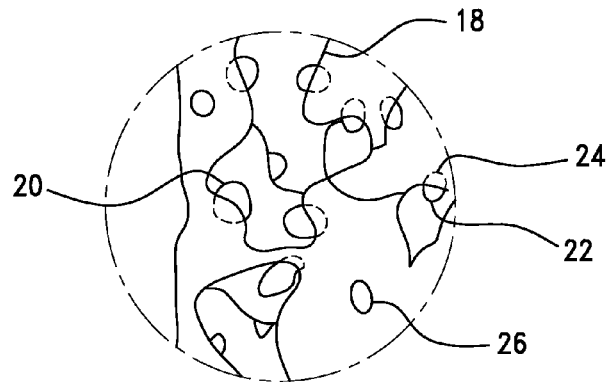
FIG. 2 is a sectional view corresponding to section A of FIG. 1.

In observing FIG. 2, while some of the hydrophilic particles 26 may be embedded and surrounded by silicone in the foam 14, some of the hydrophilic particles 20 have an anchored portion 24 firmly anchored to the pore walls 18 and an exposed portion 22 extending outwardly away from the pore wall 18 upon which the anchored portion 20 is anchored. The exposed portions 22 enable the hydrophilic particles to take up moisture while still connecting to the silicone foam and being secured to the foam.

The hydrophilic particles in the silicone foam act to absorb any moisture brought into the absorbent structure. The hydrophilic particles for use in the absorbent structure are described more fully in U.S. application Ser. Nos. 10/725,574 and 11/339,696. The hydrophilic particles preferably include absorbent powders such as product Z-1069 or Favor PAC 230 from Stockhausen-Degussa Inc.

After absorbing moisture, the hydrophilic particles may retain and store moisture in the absorbent structure, expel moisture from the absorbent structure, or both.

The absorbent structure has desirable moisture storage capacity. That is to say, the hydrophilic particles embedded in the absorbent structure have moisture storage capacity that will provide the absorbent structure of this embodiment with desirable moisture storage capacity. The hydrophilic particles effectively retain absorbed moisture and are unlikely to allow absorbed moisture to re-enter the environment where the moisture originated.

When expelling moisture, the hydrophilic particles expel moisture in the form of vapor. The vapor leaves the particles and moves up through the absorbent structure towards the surface of the absorbent structure opposing the facing layer. The moisture in the form of vapor eventually leaves the absorbent structure, thus allowing the hydrophilic particles to absorb additional moisture.

According to this embodiment, the hydrophilic particles are generally spherical. However, the shape of the hydrophilic particles is not limited to spherical shape. Moreover, hydrophilic fibers may be used in place of or in conjunction with hydrophilic particles. Hydrophilic fibers suitable for use in the absorbent structure include, but are not limited to, hydrophilic natural or synthetic fibers.

The hydrophilic particles may be uniformly distributed throughout the silicone foam. Uniform distribution of the hydrophilic particles helps to ensure that any expansion of the absorbent article caused by moisture absorption occurs uniformly throughout the structure. When an absorbent structure expands in a uniform fashion, the structure is less likely to separate from the skin outside the wound area due to a "curling" effect most often caused by uneven swelling of the absorbent structure.

As discussed above, the absorbent structure generally comprises a liquid retention portion and a skin-adherent portion. According to one variation, the pore walls of the liquid retention portion are more cross-linked than the skin-adherent portion of the silicone foam. This results in the skin-adherent portion having an elastomeric form with a tackiness that lends itself to being skin adherent. The elastomeric skin adherent portion has a soft, gel-like feel. This provides the added benefit, as in the facing layer of U.S. patent application Ser. No. 10/725,574, of gently securing to a wound or skin and allowing the absorbent structure to be gently removed therefrom. The ability to gently remove the absorbent structure from a wound both reduces the pain to a patient and also decreases the risk of traumatizing the wound during removal.

As discussed above, the absorbent structure may comprise a backing layer formed on the surface opposing the facing layer. The backing layer may be a vapor permeable, liquid impervious backing layer. Exemplary backing layers and methods for securing the same onto the absorbent structure are described in U.S. application Ser. Nos. 10/725,574 and 11/339,696 that are incorporated herein by reference, and owned by the assignee of the pending application.

By providing a vapor permeable backing layer, the absorbent structure is still capable of expelling moisture from the absorbent structure in the form of vapor as discussed above. A vapor permeable backing layer allows moisture in the form of vapor to escape the absorbent structure. The moisture storage capacity of the absorbent structure is increased when the hydrophilic particles continually release moisture in the form of vapor that passes out of the absorbent structure.

It will be noted that the backing layer may be any type of layer which provides desirable characteristics such as being vapor permeable or impermeable. The backing layer may comprise layers other than films, and may be a textile such as a stretchable knit material or unbroken loop material. The absorbent structure may be secured to such backing layers by lamination, adhesives or may be coated directed onto the surface of the backing layer. In addition, the backing layer may be a silicone or other polymeric sheet that is either or not vapor permeable. In such polymeric sheet, the sheet may provide structural reinforcement, such as by its thickness or reinforcement by a textile or other suitable material, to the silicone foam.

Figure 3:
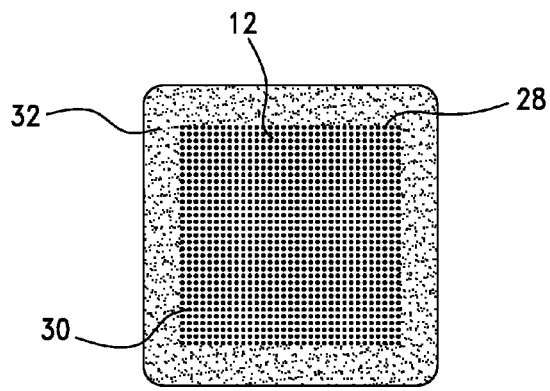
FIG. 3 is a bottom plan view of a variation of the embodiment of the absorbent article of FIG. 1.

As exemplified in FIGS. 1 and 3, the absorbent structure 10 includes a facing layer 12 that defines a plurality of apertures 28 formed and molded along one of two opposed surfaces of the absorbent structure 10. The apertures 28 may be formed in a variety of patterns and configurations, as demonstrated in FIG. 3 wherein there is an apertured region 30 and a non-apertured region 32 formed along the surface of the absorbent structure. The apertures may be formed in any of the configurations described in U.S. application Ser. No. 10/725,574.

In addition to molding the absorbent structure to comprise a plurality of apertures, the absorbent structure may also be molded such that it can accommodate devices or a portion of a device. For example, the absorbent structure may be molded to include a cavity in to which a device or a portion of a device may be inserted.

In another embodiment, a method of making the absorbent structure is disclosed. The method includes the step of providing an absorbent powder of 5%-30% of weight of the total weight of the absorbent structure in a dry condition. A wet powder is provided with about 3% w/w powder in water so as to make it easier to add water for making the foam. An uncured silicone mixture comprising part A and part B of MED-4901 from NuSil Technology, LLC in a ratio of 1:1 is mixed with the absorbent powder and the wet powder. The mixture is cured at a temperature in the range of 150° C.-200° C. for about 10 minutes. At the end of curing, a foam is formed with the absorbent powder.

In another method for making the absorbent structure, the method includes the step of providing an absorbent powder of 5%-30% of weight of the total weight of the absorbent structure in a dry condition. A wet powder is provided with about 3% w/w powder in water so as to make it easier to add water to the eventual mixture for making the foam. An uncured silicone mixture is mixed with the absorbent powder and the wet powder. The mixture is cured at a temperature at about 100° C. for about 15-20 minutes. At the end of curing, a foam is formed with the absorbent powder.

In these methods, the silicone is foamed due to the introduction of water and the high curing temperatures, as is well understood by one skilled in the art. The water evaporates during the curing of the silicone, and the absorbent powder is evenly distributed in the foam structure so as to render the resultant absorbent structure partially hydrophilic without substantially changing the functional groups of the silicone itself. The even distribution of the powder in the absorbent structure also provides the absorbent structure with the benefits described above in the previous embodiment.

The method of this embodiment may further comprise the step of applying the uncured mixture onto a mold having a plurality of projections arranged in a pattern. The curing step is performed after the uncured mixture is placed in the mold, thereby resulting in an absorbent structure having the shape of the mold once the curing step has been performed. Any curing method well known to those of ordinary skill in the art may be used in this embodiment.

The projections in the mold impart a plurality of apertures on one surface of the absorbent structure. As discussed in the previous embodiment, the pattern and configurations of the projections in the mold can be any variety of patterns and configurations, thus making the method described herein capable of producing an absorbent structure having apertures in a variety of patterns and configurations.

The method of this invention may also employ a mold which, after curing, produces an absorbent structure that can accommodate devices or portions of devices as described in the previous embodiment.

A step of securing a vapor permeable, liquid impervious backing layer on one surface of the absorbent structure may also be included in the method of this embodiment. The backing layer is preferably secured to the surface of the absorbent structure opposed to the facing layer having apertures.

The backing layer may be secured to the absorbent structure by any means known in the art, including those methods described in U.S. application Ser. Nos. 10/725,574 and 11/339,696.

The silicone foam undergoes cross-linking during the curing step. That is to say, application of heat causes the silicone mixture to cross-link. In a preferred configuration, the curing step is performed such that the pore walls of the liquid retention portion of the absorbent structure are more cross-linked than the skin-adherent portion of the silicone foam. This results in the skin-adherent portion having an elastomeric form with a tackiness that lends itself to being skin adherent. The elastomeric skin adherent portion has a soft, gel-like feel.

It will be understood that the above described embodiments and methods of the invention are illustrative in nature, and that modifications thereof may occur to those skilled in the art. Accordingly, this invention is not to be regarded as limited to the embodiments disclosed herein, but is to be limited only as defined in the appended claims.

The invention claimed is:

1. An absorbent structure comprising:
   a porous substrate having walls; and
   a plurality of hydrophilic particles anchored to the walls of the substrate, wherein a portion of the plurality of the hydrophilic particles have an anchored portion anchored to the walls and an exposed portion extending outwardly away from the wall upon which the anchored portion is anchored.

2. The absorbent structure according to claim 1, wherein the porous substrate defines opposed first and second surfaces, the first surface of the porous substrate having skin-adherent properties.

3. The absorbent structure according to claim 2, wherein a vapor permeable, liquid impervious backing layer is secured to the second surface of the porous substrate.

4. The absorbent structure according to claim 1, wherein the porous substrate has opposed first and second surfaces, the porous substrate forming a liquid retention portion within the thickness of the porous substrate, and a skin-adherent portion underlying the liquid retention portion and generally defined along the first surface of the porous substrate.

5. The absorbent structure according to claim 4, wherein the porous substrate is a cross-linked polymer, the liquid retention portion being more cross-linked than the skin-adherent portion of the porous substrate.

6. The absorbent structure according to claim 2, wherein the first surface defines a plurality of generally uniformly spaced and formed holes, the absorbent structure being monolithic.

7. The absorbent structure according to claim 1, wherein the porous substrate is hydrophobic.

8. The absorbent structure according to claim 1, wherein the porous substrate is formed from an elastomeric polymeric material.

9. The absorbent structure according to claim 1, wherein the porous substrate is formed from silicone.

10. The absorbent structure according to claim 1, wherein the porous substrate is a foamed material.

11. The absorbent structure according to claim 10, wherein the porous substrate is closed-cell foam.

12. The absorbent structure according to claim 10, wherein the porous substrate is open-cell foam.

13. An absorbent structure comprising:
    a hydrophobic porous substrate having means for moisture storage capacity, the storage capacity achieved by a plurality of hydrophilic particles anchored to the porous substrate;
    wherein a portion of the plurality of the hydrophilic particles have an anchored portion anchored to the walls and an exposed portion extending outwardly away from the wall upon which the anchored portion is anchored.

14. The absorbent structure according to claim 13, wherein the porous structure defines a plurality of walls upon which the hydrophilic particles are anchored.

15. The absorbent structure according to claim 13, wherein the porous substrate defines opposed first and second surfaces, the first surface of the porous substrate having skin-adherent properties.

16. The absorbent structure according to claim 15, wherein a vapor permeable, liquid impervious backing layer is secured to the second surface of the porous substrate.

17. The absorbent structure according to claim 13, wherein the porous substrate has opposed first and second surfaces, the porous substrate forming a liquid retention portion within the thickness of the porous substrate, and a skin-adherent portion underlying the liquid retention portion and generally defined along the first surface of the porous substrate.

* * * * *